US00PP08925P

United States Patent [19]

Van der Salm

[11] Patent Number: Plant 8,925

[45] Date of Patent: Oct. 4, 1994

[54] LILIUM PARAMOUNT

[76] Inventor: Gerardus C. Van der Salm, 35306 NW. Toenjes Rd., Woodland, Wash. 98674

[21] Appl. No.: 186,313

[22] Filed: Jan. 25, 1994

[51] Int. Cl.[5] ..... A01H 5/00

[52] U.S. Cl. ..... Plt./87.4

[58] Field of Search ..... Plt. 874

*Primary Examiner*—James R. Feyrer

[57] ABSTRACT

A new variety of hybrid lily plant bearing large upfacing flowers of excellent form and long persistence, both on the plant and as cut-flowers. The flowers of the new plant are particularly characterized by their large size and substance, their completely upfacing orientation, and particularly by their even deep pink coloration, their small green nectaries bordered with narrow yellow margins, and their inconspicuously colored papillae. This combination is completely new in the Oriental hybrid divisions of lilies suited to forcing and to mass commercial cultivation. The variety is highly resistant to Fusarium disease and shows tolerance of virus. The bulbs may be precooled and forced for cut-flower production under a wide range of light and temperature conditions. The clone is vigorous and is a good grower and propagator.

1 Drawing Sheet

BACKGROUND OF THE INVENTION

My new variety of lily plant originated as a seedling which first flowered in Woodland, Wash., in 1987. The breeding efforts had as their objective the production of large-flowered completely upfacing Oriental hybrids in a variety of shades of pink, suited to forcing into flower out of season, heretofore unknown in the lily breeding art.

I achieved the desired objective by intercrossing unnamed upright and semi-upright Oriental seedlings which carried pink flower color and were also suited to forcing for year-round use as cut-flowers. The unnamed Oriental seedings which were the parents of 'Paramount' were produced by me, from a series of crosses among seedlings which were selected in my fields from large seedling populations of my own crosses. The original crosses came from material unique to my own breeding lines and not available in the trake. The field-selected seedlings were genetically very diverse and 100 seedlings were selected for their outstanding vigor, stem length, pink flower color, and upfacing or semi-upfacing flower orientation. These were forced into flower under glass, and the 25 seedlings which showed the best forcing performance were then radonly intercorssed to produce a large quantity of seed. This seed was grown to flowering sizer, producing a large population of seedingls, from which the best 100 were again selected for vigor, stem length, pink flower color, and upfacing or semi-upfacing flower orientation. These were subsequently tested for their forcing performance, and 'Paramount' was selected as one of the seedlings best suited for forcing as a cut-flower.

The flowers of my new lily are characterized by a completely upfacing orientation, large size, unusually thick substance, even deep pink coloration, inconspicuously pigmented papillae, and small green nectaries bordered with narrow yellow margins, a combination unique among Oriental hybrid lilies. The pedicels are sharply ascending, and the buds are completely upright, which minimizes the breaking off of the buds during their handling as cut-flowers. The variety possesses unusually strong, stout stems. In addition, the clone possesses to a high degree desirable characteristics of hybrid vigor. The clone is a good grower and propagator, as observed at Woodland, Wash.

My new variety of lily plant has been asexually reproduced by me and under my driection at Woodland, Wash. Successive generations produced by natural propagation from bulblets, by bulb scale propagation, and by tissue culturing from bulb scale explants have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing, which shows the open bloom in full color and illustrates the flower form, the tepal arrangement, and in particular the novel and distinctive completely upfacing even deep pink flowers with inconspicuously pigmented papillae and small green nectaries bordered with narrow yellow margins.

DESCRIPTION OF THE NEW VARIETY

The following is a detailed description of my new variety of Oriental hybrid lily, with nomenclature according to the *International Lily Register* (Royal Horticultural Society of London, Second Edition, 1969), and with color designations according to the Colour Chart of The Royal Horticultural Society, published by the Society in 1966.

The Plant

Origin: Seedling.

Seed parent: Selected unnamed Oriental hybrid seedling.

Pollen parent: Selected unnamed Oriental hybrid seedling.

Commercial classification: Hybrid Lilium clone.

Horticultural classification: Division VII-B, bowl-shaped Oriental Hybrid lily, according to the Horticultural Classificaton of Lilies, Royal Horticultural Society of London.

Form: Single stem, erect and stately.

Height: 80 to 125 cm from bulbs 14 to 18 cm in circumference, provided their light levels are adequate; low light levels may cause "stretching."

Growth: Vigorous and upright.
Foliage quantity: Abundant.
Size of leaf: Broad, 4 to 7 cm wide×10 to 14 cm long.
Shape of leaf: Lanceolate (pointed).
Texture: Leathery and glossy.
Color: Medium to dark green, lighter on lower side.
Bulb:
*Size.*—Any size, ranging to 25 cm circumference commercially.
*color.*—White, with flushes of pink or yellow after exposure to light.

The Bud

Form: Obtuse, ovoid, and long. Buds are completely upright.
Size: 12 to 16 cm long and 10 to 14 cm in circumference just prior to opening.
Opening: Bud opens slowly, in response to morning light; this takes about one hour.
Color: Soft pink (RHS CC red-purple 57 C-D), with soft green to white midribs, base, and tip just prior to opening.
Peduncle: Averages 4 to 6 cm, but it may elongate if light levels are too low or if bulbs have been improperly stored prior to forcing. Color is medium to dark green with very light plum overlay.

The Flower

Blooming habit: Annually in medseason; flowers once and profusely.
Size: Flowers are large-sized, averaging 20 to 28 cm in diameter, reflexing at the tips on the second day to 18 to 22 cm in diameter. The tepals are broad: outer tepals are 3 to 4 cm wide, and inner tepals are 4.25 to 6 cm wide.
Borne: In a single racemic inflorescence producing 4 to 8 flowers from a bulb 14 to 16 cm in circumference.
Shape: Form a broad bowl shape by the second day after opening, with the "bowl" 5 to 6 cm deep.
Tepalage: Typical of genus Lilium, with 6 imbricated tepals.
Tepal
*Color.*—RHS CC red-purple 57A-C to 63 A-B, shading evenly with deepest pink along tepal midribs, depending upon growing temperatures and light levels. A narrow (1–4 mm) yellow margin borders the small green nectaries. The pink color may decrease with high temperatures and low light levels, and it may deepen slightly with cool temperatures and high light levels. Tepal reverse is RHS 57 B-C, shading to 63 A-B.
*Spotting.*—The tepal area parallel to the nectaries is lightly spotted with small papillae of the same color as the deeper pink portions of the flower.
*Longevity.*—Tepals stay on stems about three weeks.
Nectaries: Small green nectaries bordered with a 1–4 mm yellow margin.
Pedicel:

*Length.*—Average 6 to 10 cm long.
*Color.*—Medium to dark green with very light plum overlay.
*Form.*—Sturdy, flexible, and sharply ascending.
Color changes: Flowers become slightly lighter and a move lavender-toned pink as the flowers age. Low light levels and extreme heat may cause the pink pigmentation to decrease.
Appearance: Flower is shiny.
Disease resistance: The flower and plant are resistant to disease; in particular, they are resistant to Fusarium bulb rot and Botytis blight.
Fragrance: Light sweet fragrance.
Lasting quality: The flower is long lasting, both on the plant and as a cut-flower.

The Reproductive Organs

Stamens: Arrangement typical of genus Lilium. Six stamens with soft yellow-green to white filaments 8 to 10 cm long.
Pollen and anthers (dehisced): RHS CC greyed red 180 A to greyed purple 182 A.
Pistil: One in number, 10 to 12 cm long.
Stigma: Very light greyed green (lighter than RHS 193 D) to very light greyed purple (lighter than RHS 186 D) to white; large in size.
Characteristics of ovary: Characteristic of genus Lilium.

The Fruit

Fertility: The fruit bears fertile seed.
Shape: Ovoid.
Color at maturity: Soft brown, sometimes overlaid with soft plum.

My new variety of Oriental hybrid lily most nearly resembles 'Acapulco'(U.S. Plant No. 8,313), but its flowers are a deeper, slightly redder (less purple) pink and its papillae are smaller and inconspicuously pigmented. Its tepal reverse is also a much deeper pink than that of 'Acapulco.' Its buds are more strongly upright, and its pedicels are shorter.

I claim:

1. A new and distinctive variety of Oriental hybrid lily plant substantially as herein shown and described, characterized by its high resistance to disease; its tolerance of virus; its vigorous growth and rapid natural propagation; the excellence of its flower form, size, and substance; its versatility both as a garden plant and as a cut-flower producer from pre-cooled bulbs forced under glass out of season; and in particular by its upright buds, its sharply ascending pedicels, and by its completely upfacing flowers with even deep pink coloration, inconspicuously colored papillae, and small green nectaries bordered with narrow yellow margins, a combination unique among Oriental hybrid lilies suited to forcing and to mass commercial cultivation.

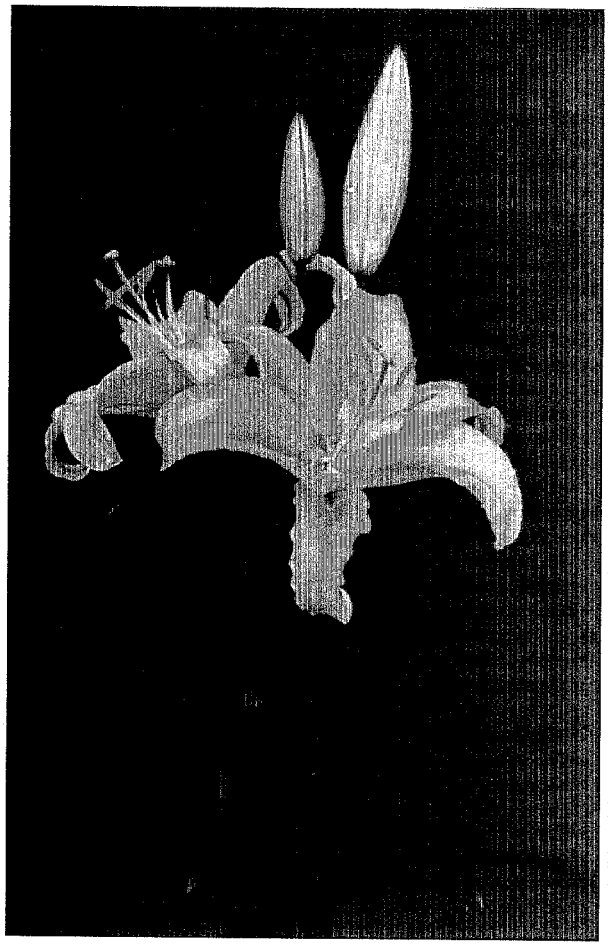

* * * * *